United States Patent [19]

Lang et al.

[11] Patent Number: 4,783,549

[45] Date of Patent: Nov. 8, 1988

[54] BENZONORBORNENE DERIVATIVES, PROCESSES FOR THEIR PREPARATION AND MEDICINAL AND COSMETIC COMPOSITIONS CONTAINING THEM

[75] Inventors: Gérard Lang, Saint-Gratien; Jean Maignan, Tremblay les Gonesse; Serge Restlé, Aulnay sous Bois; Braham Shroot, Antibes, all of France

[73] Assignee: L'Oreal, Paris, France

[21] Appl. No.: 772,525

[22] Filed: Sep. 4, 1985

[30] Foreign Application Priority Data

Sep. 5, 1984 [LU] Luxembourg .......................... 85531
Dec. 20, 1984 [LU] Luxembourg .......................... 85700

[51] Int. Cl.$^4$ ........................................... C07C 69/16
[52] U.S. Cl. ........................................ 560/104; 560/8; 560/100; 562/405; 562/490; 562/495; 568/659; 568/813; 564/172; 564/180
[58] Field of Search .............................. 560/8, 56, 100; 562/405, 490, 495; 564/172, 180; 568/659, 813

[56] References Cited

U.S. PATENT DOCUMENTS

| | | | |
|---|---|---|---|
| 4,193,931 | 3/1980 | Loeliger | 560/56 |
| 4,326,055 | 4/1982 | Loeliger | 560/8 |
| 4,439,614 | 3/1984 | Dawson | 560/8 |
| 4,578,498 | 3/1986 | Frickel | 560/8 |

OTHER PUBLICATIONS

Journal of Medicinal Chemistry, vol. 27, No. 11, Nov. 1984, ACS, pp. 1516-1531, Dawson et al.
European Journal of Medicinal Chemistry, Chimica Therapeutica, vol. 15, No. 1, 1980, pp. 9-15.
Journal of Medicinal Chemistry, vol. 23, 1980, pp. 1013-1022, Dawson et al.

Primary Examiner—Paul J. Killos
Attorney, Agent, or Firm—Cushman, Darby & Cushman

[57] ABSTRACT

A compound of formula (I)

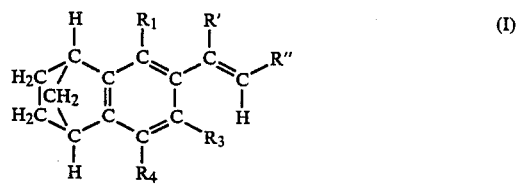

its isomers and its salts in which
—$R_1$, $R_3$ and $R_4$ are each indepenently hydrogen, $C_1$-$C_8$-alkyl, $C_1$-$C_8$-alkoxy, halogen, $C_1$-$C_8$-acyloxy or hydroxyl;
—$R'$ is hydrogen or $C_1$-$C_6$-alkyl;
—$R''$ is either a polyene chain or a benzene ring are useful in cosmetics and in the treatment of various dermatological and other complaints.

10 Claims, No Drawings

BENZONORBORNENE DERIVATIVES, PROCESSES FOR THEIR PREPARATION AND MEDICINAL AND COSMETIC COMPOSITIONS CONTAINING THEM

DESCRIPTION

The invention relates to benzonorbornenes substituted on the benzene ring, and to a process for preparing them. The invention also relates to the use of these new compounds, either in cosmetic compositions or in pharmaceutical compositions for the treatment of dermatological complaints related to a keratinization (differentiation-proliferation) disorder, for the treatment of dermatological or other complaints with an inflammatory and/or immuno-allergic component, in the treatment of the diseases of degeneration of the conjunctive tissue and of tumors, and in the treatment of rheumatoid psoriasis. Furthermore these compounds may be used in opthalomology, particularly in the treatment of corneopathies.

The therapeutic action of vitamin A in its acid, aldehyde or alcohol form is well known in dermatology (see, on this subject, the publication "Experientia", volume 34, pages 1105-1119 (1978)); this action in the treatment of cutaneous proliferations, of acne, of psoriasis and of similar complaints will be referred to hereafter by the general expression "retinoid-type action".

It has been found that products with a structure similar to that of vitamin A also have a retinoid type action, but that the secondary effect of toxic hypervitaminosis could, in the case of some compounds, be multiplied by a lower factor than the multiplication factor of the required retinoic effect (see, on this subject, Eur. J. Med. Chem.-Chimica Therapeutica, January-February 1980, 15, No. 1, pages 9-15); thus, French Patent Application Nos. 2,422,620 and 2,529,458 describe new stilbene and methylstyrylnaphthalene derivatives incorporating, on the ring on which an unsaturated substituted chain is grafted, a number of methyl groups, because the studies carried out led to the conclusion that multiplication of the methyl groups appeared to improve the therapeutic effectiveness (see the above-mentioned publication Eur. J. Med. Chem.).

Benzonorbornene and some of its derivatives were already known (see, on this subject, J. Org. Chem., 32, pages 893-901 (1967) and J. Am. Chem. Soc., 87, 21, pages 4794-4804 (1965)), but it had never been demonstrated that these benzonorbornene derivatives could have a retinoic action. Subsequently, it has been shown that some norbornene derivatives have a retinoic activity (see, on this subject, the publication J. Med. Chem. 1980, 23, pages 1013-1022 and 1981, 24, pages 1214-1223). However, in endeavoring to improve therapeutic effectiveness, the person skilled in the art, knowing that it was necessary to increase the methyl substitutions on this ring, tended to move away from benzonorbornene derivatives. Now, it has been found, according to the invention, that, surprisingly, some benzonorbornene derivatives have a particularly advantageous retinoid-type action.

The present invention provides a benzonorbornene derivative of formula (I) or an isomer or salt thereof, wherein formula (I) is

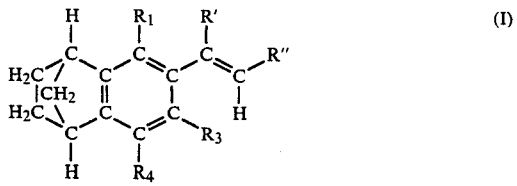

in which:
—$R_1$, $R_3$ and $R_4$ are each independently hydrogen, $C_1$-$C_8$ alkyl, $C_1$-$C_8$ alkoxy, halogen, $C_1$-$C_8$ acyloxy or hydroxyl;
—$R'$ is hydrogen or $C_1$-$C_6$ alkyl;
—$R''$ is an unsaturated group which is:
either (1) a polyene chain of formula (II)

in which $A_2$ is either a group $CH_2OR_6$ in which $R_6$ is hydrogen or $C_1$-$C_6$ alkyl or a group $COR_7$ in which $R_7$ is hydrogen, $C_1$-$C_6$ alkoxy, aryloxy, benzyloxy, a sugar residue, substituted or unsubstituted amino, $C_1$-$C_6$ alkyl or hydroxyl;
or (2) a benzene ring of formula (III)

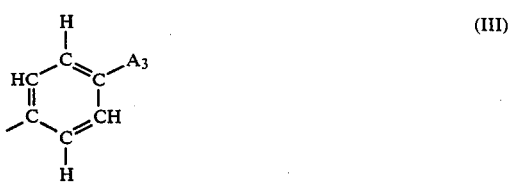

in which $A_3$ may be any of the meanings given earlier for $A_2$ or may be hydrogen, $C_1$-$C_6$ alkyl, alkylthio(—$SR_5$), alkylsulphinyl

or alkylsulphonyl (—$SO_2R_5$), wherein $R_5$ is $C_1$-$C_6$ alkyl;
provided that if $R'$ is H or methyl, $R_1=R_4=H$ and $R_3$ is H or methyl, $R''$ cannot be a group of formula (III) in which $A_3$ is —$COR_7$ in which $R_7$ is OH, alkoxy, aryloxy or —$NR_{10}R_{11}$ where $R_{10}$ is a linear or branched alkyl, substituted or unsubstituted by OH, and $R_{11}$ is H or a linear or branched alkyl, substituted or unsubstituted by OH.

When the substituent $A_2$ or $A_3$ denotes a group $COR_7$ and $R_7$ is a $C_1$-$C_6$ alkoxy radical, it is preferred that $R_7$ be a radical $OR_8$, $R_8$ being chosen from the group formed by the methyl, ethyl, propyl, isopropyl, butyl, t-butyl and hexyl radicals and by $C_1$-$C_6$ alkyl radicals substituted by one or more hydroxyls, such as 2-hydroxyethyl, 2-hydroxypropyl or the isomers of dihydroxypropyl such as 2,3-dihydroxypropyl, 1,3-dihydroxy-2-propyl, or pentaerythritol.

When the substituent $A_2$ or $A_3$ denotes a group $COR_7$ and $R_7$ is a hydroxyl, this carboxylic group can advantageously be converted to a salt. The invention also relates to salts of compounds of formula (I) e.g.

those of zinc, alkaline-earth metal, alkali metal or an organic amine such as triethanolamine.

When the substituent $A_2$ or $A_3$ is a group $COR_7$ and $R_7$ is an aryloxy group, the aryl radical of $R_7$ can advantageously correspond to the formula (IV):

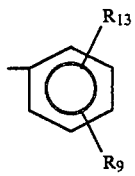 (IV)

in which $R_9$ and $R_{13}$ are each independently hydrogen, $C_1-C_4$ alkyl, hydroxyl, halogen, a trifluoromethyl or alkoxy group.

When the substituent $A_2$ or $A_3$ is a group $COR_7$ and $R_7$ is a benzyloxy group, the benzyl radical of $R_7$ can advantageously correspond to the formula (V):

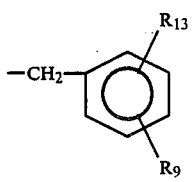 (V)

in which $R_9$ and $R_{13}$ have the same meanings as in the formula (IV).

When the substituent $A_2$ or $A_3$ is a group $COR_7$ and $R_7$ is a sugar residue, $COR_7$ advantageously originates from a glucose ester or a mannitol ester.

When $A_2$ or $A_3$ is $COR_7$ and $R_7$ is an amino of formula $NR_{10}R_{11}$, $R_{10}$ and $R_{11}$ are each independently, preferably, hydrogen, $C_1-C_6$ alkyl which is straight-chain or branched and which is substituted or unsubstituted by one or more hydroxyls, or, $R_{10}$ and $R_{11}$ taken together with the N atom to which they are attached, form a substituted or unsubstituted heterocyclic ring, one of $R_{10}$ or $R_{11}$ also being capable, when the other is hydrogen, of being aryl of formula (IV) or benzyl of formula (V), formulae in which $R_9$ and $R_{13}$ have the meanings given above. $NR_{10}R_{11}$ can also correspond to the amine function of an aminoacid or to the amine function of the glucosamine.

When R'' is a polyene chain of formula (II), if the carbon bearing the substituent $A_2$ is given the number 2, the carbon bearing the methyl substituent the number 3 and the subsequent carbon adjacent to the latter in the chain the number 4, the structures at carbons 2 and 4 may be 2-E, 4-E or 2-Z, 4-Z or 2-E, 4-Z or 2-Z, 4-E. In general, the compounds of formula (I) according to the invention may be of trans structure (structure E) or of cis structure (structure Z); the invention covers all the isomers as well as the optical isomers. Furthermore, it has to be stated that when these products are exposed to light, conversion from one type of isomer to another type may take place.

Preferred compounds of the invention are those of formula (I')

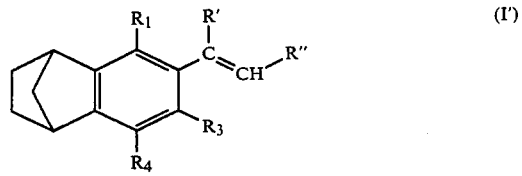 (I')

in which $R_1$, $R_3$ and $R_4$ are as defined above, R' is hydrogen or methyl, R'' is a chain of formula (II) in which $A_2$ is $—COR_7$ in which $R_7$ is hydroxy, $C_1-C_6$ alkoxy or amino; and isomers and acid salts thereof.

The invention also relates to two processes for preparing the new compounds of formula (I) and their isomers and salts. In all cases, these preparation processes employ, as a starting compound, a 2-acylbenzonorbornene of formula

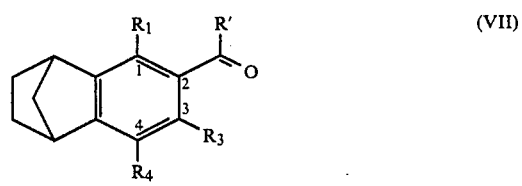 (VII)

The invention also provides a compound corresponding to the above-mentioned formula (VII), in which $R_1$, $R_3$, $R_4$ and R' have the meanings given earlier, but R' may not be H or methyl when $R_1=R_4=H$ and $R_3$ is H or methyl.

This compound of formula (VII) may be obtained in various ways, depending on the nature of the substituents, as will be indicated later.

According to a first process, the compound of formula (VII) is reacted directly with a dialkyl phosphonate of formula:

 (VIII)

in which $R_{12}$ is $C_1-C_6$ alkyl or with a triphenylphosphonium salt of formula (IX):

 (IX)

R'' having, in these two formulae, the meanings given earlier, $X^\ominus$ denoting a halide. The product may be isomerized or salified if necessary.

According to a second process the compound of formula (VII) is obtained in a first step and, in a second step, it is reduced with sodium borohydride to a secondary alcohol of formula:

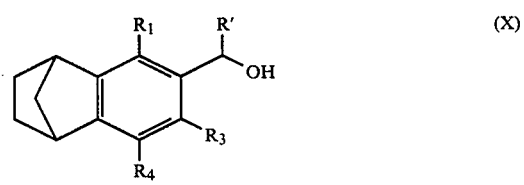 (X)

in a third step the compound of formula (X) is converted by the action of phosphorus tribromide to a bromide of formula:

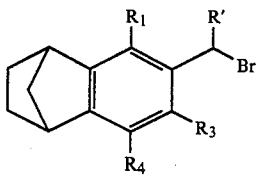

(XI)

in a fourth step, the compound of formula (XI) is treated with triphenylphosphine to obtain the triphenylphosphonium bromide of formula:

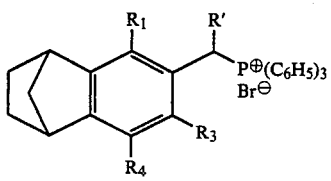

(XII)

in a fifth step the compound of formula (XII) is reacted with an aldehyde R″—CHO to obtain the compound of formula (I), R′, R″, $R_1$, $R_3$ and $R_4$ having in these formulae the meanings given earlier. The product may then be isomerized or salified if necessary.

Among the aldehydes which may be employed, mention may be made of methyl 4-formylbenzoate, which is available commercially.

As an example of an aldehyde, use has also been made of ethyl 5-formyl-3-methyl-2,4-pentadienoate, which is synthesized in two steps, as indicated in the above-mentioned publication "Experientia" 1978, 34, pages 1105–1119 (see also Chemical Abstracts 57, 2056 b and 58, 10066 e); in this process, pyruvic aldehyde dimethyl acetal and triethyl phosphonoacetate, which are both commercial products, are reacted in the presence of sodium hydride in tetrahydrofuran. This produces an unsaturated ester, which is condensed with ethyl vinyl ether in the presence of boron trifluoride etherate; the condensation product is then hydrolyzed with phosphoric acid and the aldehyde obtained is purified by recrystallization.

It should be noted that the two access routes to the product of formula (I) which form the two preparative processes mentioned above are not equivalent and need to be chosen as a function of the nature of the substituents.

To obtain the compounds of formula (VII) which serve as starting material in the two preparative processes, it is possible, in a first alternative form, to prepare, in a first step, a benzonorbornene of formula (VI):

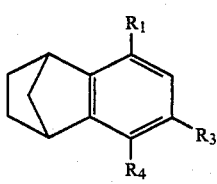

(VI)

formula in which $R_1$, $R_3$ and $R_4$ have the meanings given earlier; in a second step, the compound of formula (VI) is acylated with an acyl chloride R′COCl, in the presence of aluminium chloride, to obtain the 2-acylbenzonorbornene of formula (VII), R′ having the meanings given earlier.

According to another alternative form, in a first step, the acylation is carried out with an acyl chloride or an acid anhydride giving rise to the appearance of the group R′—CO— on the benzonorbornene ring, and then, in a second step, the substituents $R_1$, $R_3$ and $R_4$ are attached to the compound obtained, R′, $R_1$, $R_3$ and $R_4$ having the meanings given earlier.

The choice between the two abovementioned alternative ways of producing the compound of formula (VII) is made according to the nature of the substituents.

According to a third alternative form, which can also be employed when the nature of the substituents allows this, the compound of formula (VII) is obtained by carrying out, in a first step, the cycloaddition of a benzyne of formula (XXV):

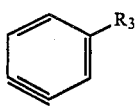

(XXV)

with cyclopentadiene, $R_3$ having the meanings given earlier; in a second step, the benzonorbornadiene of formula (XXIII):

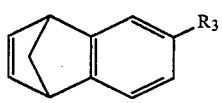

(XXIII)

thus obtained is reduced to a benzonorbornene of formula (XXIV):

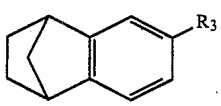

(XXIV)

in a third step, the compound of formula (XXIV) is acylated with an acyl chloride (R′COCl), in the presence of aluminum chloride, to produce the compound of formula (VII) R′ having the meanings given earlier.

By way of nonrestrictive examples of the preparative methods defined above, the access routes corresponding to some compounds of formula (VII) will be given more precisely below.

First example of access to the compounds of formula (VII):

Synthesis of the compounds of formula (VII) in which $R_1=R_4=H$; $R_3=C_1-C_8$ alkyl; and $R′=C_1-C_6$ alkyl.

As a starting material, use is made of unsubstituted 2-acylbenzonorbornenes of formula (XIV):

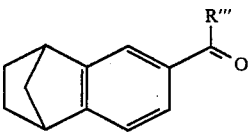

(XIV)

formula in which R′″ is defined by the fact that $R_3=R′″—CH_2$. 2-Acylbenzonorbornenes of formula (XIV) in particular are obtained by the following operating procedure:

(a) to obtain benzonorbornadiene of formula (i)

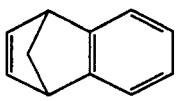
(i)

freshly distilled cyclopentadiene is reacted with benzyne of formula (ii)

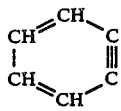
(ii)

Benzyne of formula (ii) is prepared either from 2-aminobenzoic acid of formula (iii)

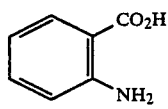
(iii)

which is treated with isoamyl nitrite, or from the organomagnesium derivative of 2-bromofluorobenzene of formula (iv)

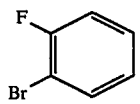
(iv)

(b) benzonorbornadiene of formula (i) is purified by distillation and then reduced by hydrogenation in the presence of palladium on charcoal, the reduction making it possible to obtain benzonorbornene of formula (v)

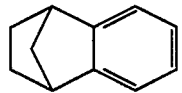
(v)

(c) benzonorbornene of formula (v) is acylated by a Friedel-Crafts reaction with acyl chloride in the presence of aluminum chloride; this acylation is selective for β and the required 2-acylbenzonorbornene of formula (XIV)

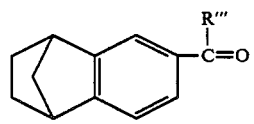
(XIV)

is obtained, which serves as a starting material in the preparative process according to the invention.

The compound of formula (XIV) is subjected to a Wolff-Kishner reduction to obtain 2-alkylbenzonorbornene of formula (XV):

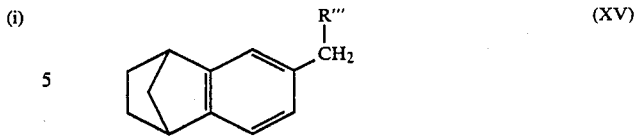
(XV)

The compound of formula (XV) is then acylated by a Friedel-Crafts reaction with an acyl chloride R'COCl, in the presence of aluminum chloride, to obtain the 2-acyl-3-alkylbenzonorbornene of formula (XVI):

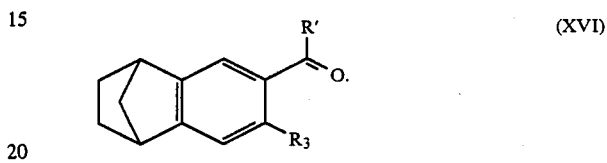
(XVI)

Second example of access to the compounds of formula (VII):

Synthesis of the compounds of formula (VII) in which $R_1$ and/or $R_4$=Br; $R_3$=$C_1$-$C_8$ alkyl or H; and $R'$=$C_1$-$C_6$ alkyl.

Use is made of the compounds of formulae (XVI) or (XIV) prepared beforehand, and they are treated directly with one or two equivalents of bromine in the presence of aluminum bromide; the mono- or dibrominated 2-acylbenzonorbornene, optionally alkylated in the 3 position, of formula (XVII):

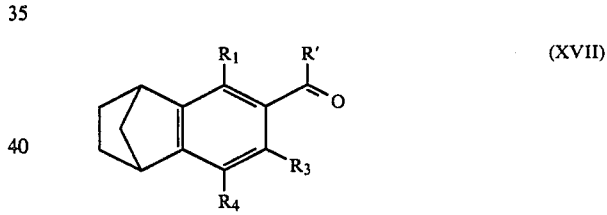
(XVII)

is thus obtained.

Third example of access to the compounds of formula (VII):

Synthesis of the compounds of formula (VII) in which $R_1$=$R_4$=$C_1$-$C_8$ alkoxy and $R_3$=H or $C_1$-$C_8$ alkyl.

Use is made, as a starting material, of 1,4-dihydroxybenzonorbornene of formula (XIX):

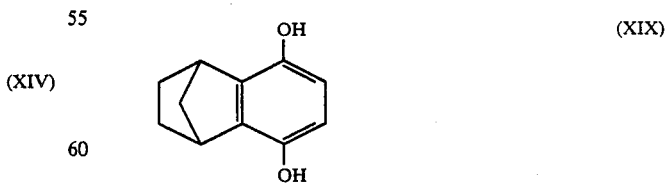
(XIX)

This commercial product is subjected, in a basic medium, to an alkylation with an alkyl halide R'''X, where X is a halogen atom and R''' is defined by the fact that $R_1$=$R_4$=OR'''. In this way a 1,4-dialkoxybenzonorbornene of formula (XX):

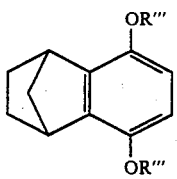

is obtained.

The compound of formula (XX) is then acylated with an acyl chloride R'COCl in the presence of aluminum chloride to obtain a 2-acyl-1,4-dialkoxybenzonorbornene of formula (XVIII)

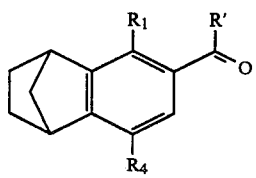

formula where R' has the meanings given for the formula (I)

By way of additional information it may be mentioned that the compound of formula (XVIII) may be employed to obtain compounds of formula (I) by being condensed directly with compounds of formula (VIII) or (IX), that is to say by making use of the first preparative process.

Fourth example of access to the compounds of formula (VII):

Synthesis of the compounds of formula (VII) in which $R_1=R_4=C_1-C_8$ alkoxy and $R_3=C_1-C_8$ alkyl.

The compound of formula (XVIII) is used as a starting material. The acyl group of the compound of formula (XVIII) is reduced to a corresponding alkyl group to obtain the compound of formula (XXVI):

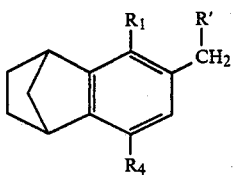

The trisubstituted benzonorbornene of formula (XXVI) is acylated with an acyl chloride R'COCl, in the presence of aluminum chloride, to obtain a 2-acyl-3-alkyl-1,4-dialkoxybenzonorbornene of formula (VII), R' being defined by the fact that $R_3=CH_2R'$.

It has been found that the compounds of formula (I) their isomers and their salts have a retinoid type action and are particularly suitable for treating the dermatological complaints related to a keratinization (differentiation-proliferation) disorder, and dermatological or other complaints with an inflammatory and/or immuno-allergic component, particularly for treating common, comedonian or polymorphous acnes, senile or solar acnes, medicamentous or occupational acnes, extensive and/or severe forms of psoriasis and other keratinization disorders, particularly ichthyosis and ichthyosiform states, Darier's disease, palmo-plantar keratosis, leucoplasias and leucoplasiform states, lichen planus, and all benign or malignant, severe or extensive dermatological proliferations; they are also active against rheumatoid psoriasis; they can be advantageously used in dystrophic epidermolysis bullosa and in the molecular pathology of collagen; they also find a use in UV induced carcinomas (solar carcinogens), in epidermodysplasia verruciformis and apparent epidermodysplasia. They further have an application in ophthalmology and particularly in relation to corneopathies. As a result, the invention also covers medicinal compositions containing these compounds.

These compounds show good activity in the ornithine decarboxylase (ODC) inhibition test after induction by "tape stripping" in the hairless rat (Dermatologica 169, No. 4 (1984) "A Rapid and Simple Test System for the Evaluation of the Inhibitory Activity of Topical Retinoids on Cellotape Stripping Induced ODC Activity in the Hairless Rat" M. Bouclier et al.). This test is recognised as a measurement of the action of retinoids on the cellular proliferation phenomena.

The compounds also show activity in the differentiation test of cells of embryonic terato-carcinomas of mice (cells Fg): "Cancer Research" 43, p. 5268 (1983).

The compounds have an excellent comedolytic activity in the test on the Rhino mouse described by Bonne et al. in the International Journal of Cosmetic Science 3, 23-28 (1981). This testing is carried out on the skin of the Hairless Rhino mouse, recommended by Van Scott in 1972 as a model for screening comedolytic agents and based on the histological picture.

The present invention consequently also relates to a composition suitable for pharmaceutical use, intended particularly for the treatment of the above-mentioned complaints, which comprises, in a pharmaceutically acceptable carrier, at least one compound of formula (I), and/or one of its isomers and/or one of its salts.

When these compounds are employed by topical administration it is observed that they have a good activity over a very wide range of dilution; in particular, use can be made of concentrations of active compound(s) ranging from 0.0005% to 2% by weight. It is possible, of course, to employ higher concentrations when this is required for a particular therapeutic application; however, the preferred concentrations of active principle are from 0.002 to 1% by weight.

The topical compositions are advantageously in the form of ointments, salves, tinctures, creams, emulsions, solutions, lotions, sprays, powders, gels, suspensions, patches or saturated pads. The compounds are mixed with inert, nontoxic, generally liquid or pasty bases which are suitable for treatment by a topical route.

The compounds may be employed by an enteral route. By the oral route the compounds are administered in a proportion of approximately 2 μg up to 2 mg per day and per kg of the body weight; an excessive dosage may appear in the form of a hypervitaminosis A recognizable by its symptoms and capable of suggesting a hepatic toxicity requiring a biological control of the hepatic function. The required dosage may be administered as one or more doses. For administration by the oral route, the suitable forms are, for example, tablets, gelatin capsules, coated tablets, syrups, suspensions, solutions, powders, granules or emulsions; a preferred mode of administration consists in using gelatin capsules containing from 0.1 mg to approximately 1 mg of active substance(s).

The compounds may also be administered by parenteral route in the form of solutions or suspensions for perfusions or intravenous or intramuscular injections. In this case, the compounds are advantageously administered in a proportion of approximately 2 μg up to 2 mg per day and per kg of body weight; in general, parenteral administration is carried out in a proportion of 0.01 mg to 1 mg of active substance(s) per ml.

When the compounds of the invention are administered by an ocular route, they are advantageously presented in the form of a solution or a powder to be diluted to give an eye lotion.

Depending on the forms employed, the pharmaceutically acceptable base can contain, for example, water, gelatin, lactose, starch, talc, vaseline (liquid petrolatum), gum arabic, polyalkylene glycols, and magnesium stearate. The tablets, powders, granules, coated tablets or gelatin capsules may contain binders, fillers or pulverulent bases; the solutions, creams, suspensions, emulsions or syrups may contain diluents, solvents or thickeners.

The compounds of formula (I) their isomers and their salts, also find an application in the cosmetic field, in particular in body hygiene and hair care and, in particular, in the treatment of acne, seborrheas, for regrowth of hair, for combating hair loss, for combating the oily appearance of the skin or hair, or for treating physiologically dry skins. They can also be used for curing and preventing the harmful effects of sunlight.

The present invention consequently also provides a cosmetic composition containing, in a cosmetically acceptable carrier, at least one compound of formula (I) one of its salts or isomers, this composition being in particular in the form of a lotion, gel, cream, soap or shampoo.

The concentration of the compound(s) in these cosmetic compositions is generally from 0.0005% to 2% by weight and, preferably, from 0.01% to 1% by weight relative to the total weight of the composition.

In the treatment of the above-mentioned disorders, these compounds which are employed in the compositions act by increasing the epithelial follicular production of nonadhesive cells, thus displacing and expelling the contents of the acne comedon. These compounds reduce the size of the sebaceous glands and partially inhibit sebum secretion.

The compositions may contain inert or even pharmacodynamically or cosmetically active additives, and particularly:

hydrating agents such as thiamorpholinone and its derivatives, or urea;

antiseborrheic or antiacne agents, such as those described in French Pat. Nos. 1,472,021, 1,505,874, 1,560,250, 2,002,461, 2,035,799, 2,011,940, 2,060,407, 2,126,996, 2,133,991, 2,133,992, 2,139,876, 2,158,018, 2,296,406, 2,428,436, 2,468,362, 2,446,277, 2,447,187 and U.S. Pat. No. 2,332,418 and, in particular, S-carboxymethylcysteine, S-benzylcysteamine, their salts and their derivatives, thioxolone, or benzoyl peroxide;

antibiotics such as erythromycin and its esters, for example those described in U.S. Pat. No. 2,862,921 or French Patent Application No. 85/05,785, neomycin, tetracyclines or 4,5-polymethylene-3-isothiazolinones such as those described in French Pat. No. 2,492,376;

agents promoting the regrowth of hair, such as minoxidil(2,4-diamino-6-piperidinopyrimidine 3-oxide) and its derivatives, diazoxide(3-chloromethyl-1,2,4-benzothiadiazine-1,1-dioxide), phenytoin(5,5-diphenyl-2,4-imidazolidinedione), oxypropanium iodide or anthralin and its derivatives;

antiinflammatory (steroid and non-steroid) agents;

carotenoids and, in particular, β-carotene;

antipsoriatic agents such as eicosa-5,8,11,14-tetraynoic and 5,8,11-triynoic acids, their esters and their amides, anthralin and its derivatives, such as those described in French Pat. Nos. 2,113,952, 2,492,372, 2,492,373, 2,495,934, 2,499,556, or French Patent Applications Nos. 84/09,203 and 84/10,324, or U.S. Pat. No. 4,299,846, naphthalene and naphthoquinone derivatives such as those described in U.S. Pat. No. 4,299,478, European Pat. No. 7985 or in J.I.D. 84 (4) 358 (1985).

The compositions can also contain flavoring agents, preserving agents, stabilizers, moisture-controlling agents, pH-controlling agents, agents modifying osmotic pressure, emulsifiers, UV-A and UV-B screens such as those described in French Pat. Nos. 1,179,387 or 2,528,420, and antioxidants such as α-tocopherol, butylated hydroxyanisole or butylated hydroxytoluene.

The present invention will be further described by the following Examples.

Examples a, b and c describe preparative steps preceding the steps which are an integral part of the preparative process according to the invention.

Examples A and D to H illustrate the preparation of a number of compounds of formula (VII).

Examples B and C illustrate the preparation of the precursors of compounds of formula (VII).

EXAMPLE a

Preparation of 2-acetylbenzonorbornene (formula (XIV) with R'''=CH$_3$)

First step: preparation of benzonorbornadiene (formula (i))

10 g of magnesium turnings which are covered with approximately 75 cm$^3$ of anhydrous tetrahydrofuran are placed in a round flask fitted with a condenser, a thermometer, a nitrogen inlet, a dropping funnel, and protected from atmospheric moisture by a calcium chloride tube. 25 cm$^3$ of a solution, prepared beforehand, of 65 g of ortho-fluorobromobenzene and 26 g of cyclopentadiene in 200 cm$^3$ of anhydrous tetrahydrofuran are then added. The formation of the organomagnesium compound is initiated by heating the reaction mixture locally with a hairdryer, and the solvent is then kept at boiling point by dropwise addition of the remaining solution. The whole addition is completed in approximately 1 hour. The mixture is then filtered at ambient temperature and the solution is concentrated under reduced pressure. The solution is taken up again in ether and the ether phase is washed with ammonium chloride, separated by gravity and dried over magnesium sulphate; the solvent is then removed by evaporation under vacuum. The residue is then distilled and benzonorbornadiene, whose boiling point is 82°–83° C. at a pressure of 16 millibars, is obtained in a yield of 40%.

Second step: preparation of benzonorbornene (formula V)

4 g of a catalyst containing 10% of palladium on charcoal are added to a solution of 40 g of benzonorbornadiene in 400 cm$^3$ of nitrogen-degassed methanol. Nitrogen is again bubbled into this mixture and the heterogeneous solution is stirred for three hours at a gauge pressure of hydrogen of 2 bars. The mixture is then filtered, concentrated under reduced pressure and benzonorbornene is purified by distillation; its boiling point at 22.5 millibars is 86° C. 33 g of a product whose nuclear magnetic resonance spectrum corresponds to the expected structure are obtained.

Third step: preparation of 2-acetylbenzonorbornene (formula XIV with R'''=CH$_3$)

30 cm$^3$ of acetyl chloride are added to a solution of 30 g of benzonorbornene in 400 cm$^3$ of carbon disulphide and then 10.5 g of anhydrous aluminum chloride are added gradually in small quantities over approximately 2 hours. At this stage, the complete conversion of the starting product is checked by thin-layer chromatography. The reaction mixture is then poured into two liters of ice water and then neutralized with sodium bicarbonate. After three extractions with ether, the ether phase is dried over sodium sulphate and then concentrated. 38 g of an orange oil which corresponds to the expected product are obtained.

EXAMPLE b

Synthesis of 1-(5,8-methano-5,6,7,8-tetrahydro-2-naphthyl)ethyltriphenylphosphonium bromide (formula XII with R$_1$, R$_3$, R$_4$=H and R'=CH$_3$)

15 g of 2-acetylbenzonorbornene are dissolved in 75 cm$^3$ of methanol cooled to 0° C. 3 g of sodium borohydride are added in small portions and stirring is continued for 1 hour. When the starting material has been converted (which is checked by thin-layer chromatography), the reaction mixture is concentrated to half its volume and is poured into approximately 250 cm$^3$ of 1N hydrochloric acid. The product is extracted twice with ether. The organic phase is dried over magnesium sulphate and concentrated under reduced pressure. The $^1$H nuclear magnetic resonance spectrum agrees with the expected structure. The 14 g of alcohol obtained in this way are dissolved in 75 cm$^3$ of dichloromethane. 6 cm$^3$ of phosphorus tribromide are added dropwise at 0° C. Stirring is continued and the temperature is maintained at 0° C. for approximately 2 hours; the reaction mixture is then poured into 300 cm$^3$ of ice water and is extracted with dichloromethane. The organic phase is washed with a sodium bicarbonate solution, dried and concentrated under reduced pressure. 15 g of bromo derivative are recovered. The $^1$H nuclear magnetic resonance spectrum agrees with the expected structure. The product obtained in this way is dissolved in 150 cm$^3$ of anhydrous toluene. 16 g of triphenylphosphine are added and the reaction mixture is refluxed in toluene for 24 hours. After cooling, the expected product separates as an oil and crystallizes in ether.

27 g of triphenylphosphonium salt are recovered, i.e. an overall yield of 65%.

Molecular mass found: 513.

Melting point: 156°–158° C.

EXAMPLE c

Synthesis of ethyl 5-formyl-3-methyl-2,4-pentadienoate

First step: synthesis of ethyl 3-dimethylacetalisocrotonate 24 g of 50% weight strength sodium hydride, previously washed with hexane, suspended in 500 cm$^3$ of anhydrous tetrahydrofuran are added, in an inert atmosphere, into a two-liter reactor fitted with a mechanical stirrer. The suspension is cooled to 0° C. and approximately 1 cm$^3$ of crown ether (15-crown-5) is added. A solution of 112 g of triethyl phosphonoacetate and of 59 g of pyruvic aldehyde dimethyl acetal in 200 cm$^3$ of anhydrous tetrahydrofuran is added dropwise while the temperature is maintained below 20° C. Evolution of gas and thickening of the reaction mixture are observed. After the addition (approximately 2 hours), stirring is continued for 1 hour at ambient temperature. The solution is poured into approximately 1 liter of ice water and extracted with ether. The organic phase is washed with a solution of sodium chloride, dried and concentrated under reduced pressure. The expected product is purified by distillation under reduced pressure: it boils at 50°–53° C. at a pressure of 0.13 millibar. 77 g of a mixture (20/80) of cis-trans isomers are recovered (determination by $^1$H nuclear magnetic resonance), corresponding to a yield of 82%.

Second step: synthesis of the 5-formyl-3-methyl-2,4-pentadienoate 75 g of the product obtained in the first step are dissolved in 500 cm$^3$ of anhydrous hexane in a 1-liter round flask and the solution is heated to 40° C. 1.8 cm$^3$ of boron trifluoride diethyletherate are added and 30 cm$^3$ of ethyl vinyl ether are added in an inert atmosphere while the temperature is maintained below 50° C. After addition, stirring is continued for 1 hour at 40°–50° C. 10 g of sodium bicarbonate are added, are filtered off and the liquid is concentrated under reduced pressure. The residue thus obtained is taken up with 350 cm$^3$ of ethyl acetate. This solution is introduced into a round flask containing 60 g of orthophosphoric acid and 250 cm$^3$ of distilled water. The reaction mixture is heated to the reflux temperature of ethyl acetate (70°–75° C.) for 5 hours with intensive stirring and then concentrated under reduced pressure and extracted with 500 cm$^3$ of toluene. The organic phase is washed with a sodium bicarbonate solution and then dried and concentrated under reduced pressure. 47 g of crude crystalline product are obtained. After recrystallization from hexane, 28 g of pure product corresponding to the trans-trans structure are obtained.

The molecular mass found is 169. The melting point is 49°–50° C.

EXAMPLE A

Preparation of 2-isobutyrylbenzonorbornene 48.6 cm$^3$ of isobutyric anhydride are added to a solution of 35 g of benzonorbornene in 600 cm$^3$ of methylene chloride. 77.8 g of aluminum chloride in solid form are then added in small portions at a temperature of approximately 10° C.

The reaction is exothermic and the temperature of the mixture is maintained at about 10° C. The solution, originally colorless, becomes brown. When all the aluminum chloride has been added, thin-layer chromatography (TLC) is used to check that benzonorbornene has been completely converted. The reaction mixture is then poured into 1 liter of ice water. The organic phase is separated by gravity, washed with sodium bicarbonate and dried over magnesium sulphate.

The solvent is distilled off under reduced pressure. 53 g of 2-isobutyrylbenzonorbornene are obtained, the nuclear magnetic resonance spectrum of which agrees with the expected structure.

EXAMPLE B

Preparation of 2-isobutylbenzonorbornene 40 g of 2-isobutyrylbenzonorbornene obtained in Example A and 80 cm$^3$ of hydrazine in 500 cm$^3$ of butanol are placed in a round flask fitted with a condenser with a Dean-Stark water separator. The mixture is heated to 150° C. The water-butanol azeotrope distils over. When the theoretical quantity of water (43 cm$^3$) has been removed, thin-layer chromatography is used to check that 2-isobutyrylbenzonorbornene has been converted to the corresponding hydrazone. Butanol is then removed by distillation under vacuum. The crude hydrazone is taken up with 500 cm$^3$ of diethylene glycol, to which 20 g of potassium hydroxide are added. The solution obtained is then heated at 220° C. for 15 hours.

The reaction mixture is then poured into 2 liters of ice water, to which 300 g of ammonium chloride are added.

This solution is then extracted three times with 350-cm$^3$ portions of ethyl ether. The ether phases are combined, washed with water, dried over magnesium sulphate, and the solvent is removed by vacuum evaporation. 36.5 g of 2-isobutylbenzonorbornene are obtained and purified by distillation at a pressure of 23 millibars. The boiling point at this pressure is 136° C. The nuclear magnetic resonance spectrum and thin-layer chromatography show that the product obtained (30 g) is pure.

EXAMPLE C

Preparation of 2-ethylbenzonorbornene

A solution of 20 g of 2-acetylbenzonorbornene (prepared in the third step of Example (a) above) and of 10 cm$^3$ of hydrazine hydrate in 100 cm$^3$ of butanol is heated at the boiling temperature of butanol. The butanol-water azeotrope is distilled off, and then butanol is evaporated off under reduced pressure.

The crude hydrazone thus obtained is dissolved directly in 100 cm$^3$ of ethylene glycol, to which 5 g of potassium hydroxide are added and the whole is heated at the reflux temperature of ethylene glycol until the hydrazone is completely converted.

The reaction mixture, at ambient temperature, is poured into water and 2-ethylbenzonorbornene is extracted with methylene chloride. The methylene chloride phase is washed with sodium bicarbonate, dried over sodium sulphate and concentrated. After evaporation of methylene chloride 15 g of 2-ethylbenzonorbornene are obtained, which are employed in the crude state for the following acylation reactions:

EXAMPLE D

Preparation of 2-acetyl-3-isobutylbenzonorbornene (formula VII in which $R_3$=isobutyl, $R_1$=$R_4$=H, $R'$=$CH_3$)

24 g of aluminum chloride are added in small portions to a solution of 30 g of 2-isobutylbenzonorbornene (prepared according to Example B) in 500 cm$^3$ of anhydrous methylene chloride and 12.8 cm$^3$ of acetyl chloride, cooled to a temperature in the region of 10° C., while this temperature is maintained.

At the end of addition, thin-layer chromatography is used to check that all the starting material has been converted. The reaction mixture is treated as in Example A above and 35 g of 2-acetyl-3-isobutylbenzonorbornene are obtained.

EXAMPLE E

Preparation of 2-acetyl-3-ethylbenzonorbornene (Formula VII in which $R_1$=$R_4$=H, $R_3$=ethyl, $R'$=$CH_3$)

2-Ethylbenzonorbornene prepared according to Example C is treated with acetyl chloride and aluminium chloride in methylene chloride under the same conditions as 2-isobutylbenzonorbornene in Example D above.

2-Ethylbenzonorbornene is converted quantitatively to 2-acetyl-3-ethylbenzonorbornene.

EXAMPLE F

Preparation of 2-acetyl-1,4-dibromobenzonorbornene (Formula VII in which $R_1$=$R_4$=Br, $R_3$=H, $R'$=$CH_3$)

14.3 g of aluminium chloride are added to a solution of 10 g of 2-acetylbenzonorbornene in 130 cm$^3$ of anhydrous methylene chloride, cooled at 0° C., followed by a dropwise addition of 5 cm$^3$ of bromine dissolved in 40 cm$^3$ of methylene chloride. The solution is then stirred for 48 hours at ambient temperature. At this stage most of the starting material has been converted.

300 cm$^3$ of water are then added to the reaction mixture. The methylene chloride solution is separated by gravity, washed with water containing bicarbonate, dried over sodium sulphate and concentrated. 18 g of a crude product are obtained and purified by passing through a column of silica gel. The expected product is eluted with a 95/5 hexane/ethyl acetate mixture.

After concentration of the eluate phases, 15 g of 2-acetyl-1,4-dibromobenzonorbornene are obtained, the nuclear magnetic resonance spectrum of which agrees with the structure.

EXAMPLE G

Preparation of 2-acetyl-1,4-dimethoxybenzonorbornene 45 g of 1,4-dihydroxybenzonorbornene are added to a solution of 60 g of potassium tert-butylate in 200 cm$^3$ of anhydrous dimethyl sulphoxide, which is stirred at ambient temperature and protected from atmospheric moisture. After approximately 1 hour 36 cm$^3$ of methyl iodide are then added dropwise.

The reaction is exothermic and the temperature is maintained between 20° and 30° C. by means of an ice bath. Thin-layer chromatography is then used to check that the reaction is complete.

The reaction mixture is then poured into 300 cm$^3$ of water and extracted twice with ether. The ether phase is washed with water, dried over sodium sulphate and concentrated. 44 g of 1,4-dimethoxybenzonorbornene are obtained and used directly for the following acylation reaction.

23.5 g of aluminum chloride are added in small portions to a mixture of 30 g of 1,4-dimethoxybenzonorbornene and 13.8 g of acetyl chloride in 300 cm$^3$ of methylene chloride. At this stage, a check is made that all the starting material has been converted. The reaction mixture is poured into 300 cm$^3$ of water. The organic phase is washed with sodium bicarbonate, then with water, and dried over magnesium sulphate.

After evaporation of the solvent under reduced pressure 28 g of 2-acetyl-1,4-dimethoxybenzonorbornene are obtained.

EXAMPLE H

Preparation of 2-ethyl-1,4-dimethoxybenzonorbornene 1'-triphenylphosphonium bromide 2-Acetyl-1,4-dimethoxybenzonorbornene of Example G is reduced with sodium borohydride to the corresponding alcohol. This alcohol is converted quantitatively to a bromo derivative by reaction with PSr$_3$ and the triphenyl phosphonium salt is obtained by heating this bromo derivative in the presence of an equivalent of triphenylphosphine in toluene.

The salt obtained is a crystalline material which melts between 160° and 165° C. (slight decomposition commencing at 130° C.).

EXAMPLE I

Preparation of 2-formylbenzonorbornene (Formula (VII) in which $R_1=R_3=R_4=R'=H$) from benzonorbornene according to an operating procedure described in "Organic syntheses" Collective Vol. V—p. 49, which deals with the formylation of 2,4,6-trimethylbenzaldehyde 9 cm³ of titanium tetrachloride (0.082 mole) are added to a solution of 5.91 g (0.041 mole) of benzonorbornene in 50 cm³ of anhydrous dichloromethane stirred at 0° C., followed, dropwise, by a solution containing 3.2 cm³ of dichloromethyl methyl ether (0.04 mole) in 10 cm³ of anhydrous dichloromethane. The temperature is maintained at 0° C. throughout the addition and then the reaction mixture is allowed to return to ambient temperature. It is then poured onto 60 g of melting ice and extracted with 60 cm³ of dichloromethane. The organic phase is separated by separated by gravity, washed three times with 400-cm³ portions of water, drie over sodium sulphate and concentrated. 2-Formylbenzonorbornene is then purified by distillation at a pressure of 0.027 bar (20 mm Hg). It is a colourless liquid (B.p.≃144° C.-147° C./0.027 bar).

EXAMPLE J

Preparation of 2-methylbenzonorbornene triphenylphosphonium bromide

The phosphonium salt is obtained according to the same operating procedure as that described for Example H. After reduction, bromination and treatment with triphenylphosphine, 2-formylbenzonorbornene leads to a crystalline product which melts between 185° and 190° C.

EXAMPLE 1

Synthesis of all-trans ethyl 7-(5,8-methano-5,6,7,8-tetrahydro-2-naphthyl)-3-methyl-2,4,6-octatrienoate (compound of formula (I) in which $R_1$, $R_3$, $R_4$ are hydrogens, $R'=CH_3$, and $R''$ is a polyene chain, $A_2$ having the meaning $COOC_2H_5$)

20 cm³ of n-butyllithium (1.6M) are added dropwise in an inert atmosphere to a suspension of 10.25 g (0.02M) of the bromide prepared in Example b in 100 cm³ of anhydrous ether. After the intensely red solution has been stirred for 2 hours at ambient temperature, 3 cm³ of dichloromethane are added to destroy excess butyllithium and 3.3 g of the ethyl ester prepared in Example C, dissolved in 20 cm³ of dichloromethane, are added under protection against light. Stirring is continued for 2 hours at ambient temperature. The reaction mixture is poured into 150 cm³ of an ammonium chloride solution and extracted with three times 100 cm³ of ether. The organic phase is dried over magnesium sulphate and concentrated under reduced pressure. A yellow oil is obtained which is purified by being passed through a column of silica gel (eluent: 95/5 hexane/ethyl acetate). 3.9 g of a yellow oil are obtained, yeilding, after crystallization from a hexane/methanol mixture, 2.1 g (31%) of the expected all-trans ester. The ¹H 250 MHz nuclear magnetic resonance spectrum agrees with the expected structure.

Molecular mass found: 322.
Melting point: 78°-80° C.

EXAMPLE 2

Synthesis of all-trans 7-(5,8-methano-5,6,7,8-tetrahydro-2-naphthyl)-3-methyl-2,4,6-octatrienoic acid (compound of formula (I) in which $R_1$, $R_3$, $R_4$ are hydrogens, $R'=CH_3$, $R''$ is a polyene chain, in which $A_2$ has the meaning COOH)

1.5 g of the ethyl ester of Example 1 are dissolved, while protected against light, in 20 cm³ of ethanol at 50° C. 20 cm³ of a 6N aqueous potassium hydroxide solution are added and the mixture is stirred for 3 hours while the temperature is maintained at 50° C. Methanol is evaporated off under reduced pressure and the aqueous phase is acidified with 2N hydrochloric acid. A precipitate is formed, which is extracted with ether. The organic phase is dried over magnesium sulphate and concentrated under reduced pressure. The expected product crystallizes from hexane. 1.1 g of pure product are obtained (yield: 80%).

Molecular mass found: 294.
Melting point: 181° C.

Analysis of the product obtained gives the following results:

| Analysis | C | H | O |
|---|---|---|---|
| Theory | 81.59 | 7.53 | 10.87 |
| Found | 81.46 | 7.56 | 10.66 |

EXAMPLE 3

Synthesis of N-ethyl all-trans 7-(5,8-methano-5,6,7,8-tetrahydro-2-naphthyl)-3-methyl-2,4,6-octatrienoamide (compound of formula (I) in which $R_1$, $R_3$, $R_4$ are hydrogens, $R'=CH_3$, $R''$ is a polyene chain, in which $A_2$ has the meaning $CONHC_2H_5$)

200 mg of the product of Example 2 are dissolved in approximately 5 cm³ of anhydrous toluene at 50° C. 65 mg of phosphorus trichloride are added and the temperature is maintained at 45°-50° C. for 15 minutes. The yellow solution thus obtained is added dropwise, undr protection against light, to a solution of 5 cm³ of ethylamine in 20 cm³ of anhydrous toluene. During the addition, the temperature of the reaction mixture is maintained below 10° C. After one night at ambient temperature the solution is poured into 100 cm³ of water and extracted with ether. The organic phase is washed and dried and then concentrated under reduced pressure. The residue is purified by chromatography on silica gel (eluent=50/50 hexane/ethyl acetate). After recrystallization from hexane 150 mg of the expected product are recovered in the form of a white powder.

Molecular mass found: 321.
Melting point: 129° C.

Analysis of the product obtained gives the following results:

| | C | H | N | O |
|---|---|---|---|---|
| Calculated for $C_{22}H_{27}O$ | 82.31 | 8.48 | 4.36 | 4.98 |

-continued

| | C | H | N | O |
|---|---|---|---|---|
| Found | 82.24 | 8.41 | 4.36 | 5.22 |

EXAMPLE 4

Synthesis of trans-5,8-methano-5,6,7,8-tetrahydro-2-($\beta$-methylstyryl)naphthalene (compound of formula (I) in which $R_1$, $R_3$, $R_4$ are hydrogens, $R' = CH_3$, $R''$ denotes a benzene ring, $A_3$ having the meaning H)

1.55 cm$^3$ of benzaldehyde and 4.2 g of potassium carbonate are added to a suspension of 7.5 Ag of the bromide of Example b, in 75 cm$^3$ of isopropanol The reaction mixture is heated to reflux for 3 hours and then filtered on sintered glass and concentrated under reduced pressure. 4.2 g of a colorless oil are obtained, which is purified by chromatography on silica gel (eluent=95/5 hexane/ethyl acetate). 2 g of an oil are obtained, which crystallizes in isopropanol in the freezer.

Molecular mass found: 260.
Melting point: 33° C.
Analysis of the product obtained gives the following results:

| Analysis | C | H |
|---|---|---|
| Theory | 92.26 | 7.74 |
| Found | 92.24 | 7.79 |

EXAMPLE 5

Synthesis of trans-5,8-methano-5,6,7,8-tetrahydro-2-(4'-methyl-$\beta$-methylstyryl)naphthalene (compound of formula (I) in which $R_1$, $R_3$, $R_4$ are hydrogens, $R' = CH_3$, $R''$ denotes a benzene ring, $A_3$ having the meaning $CH_3$)

1.70 cm$^3$ of toluylaldehyde and 4.2 g of potassium carbonate are added to a suspension of 7.5 g of the bromide of Example b, in 70 cm$^3$ of isopropanol. The reaction mixture is heated to the reflux temperature of isopropanol for 4 hours and then filtered on sintered glass and concentrated under reduced pressure. 2.3 g of a colorless oil are obtained after chromatography on silica gel (eluent=hexane). The product crystallizes in isopropanol in the freezer. The $^1H$ nuclear magnetic resonance spectrum corresponds to the expected trans structure.

Molecular mass found: 274.
Melting point: 59° C.

EXAMPLE 6

Synthesis of trans-5,8-methano-5,6,7,8-tetrahydro-2-(4'-methylsulphonyl-$\beta$-methylstyryl)naphthalene (compound of formula (I) in which $R_1$, $R_3$, $R_4$ are hydrogens, $R' = CH_3$, $R''$ denotes a benzene ring, $A_3$ having the meaning $SO_2CH_3$)

1.8 g of 4-methylsulphonylbenzaldehyde and 2.90 g of potassium carbonate are added to a suspension of 4.2 g of the bromide of Example b in 60 cm$^3$ of isopropanol. The reaction mixture is heated to the reflux temperature of isopropanol for 4 hours and then filtered on sintered glass. 1.65 g of a product which crystallizes in the filtrate are recovered. The product is purified by chromatography on silica gel (eluent=dichloromethane). 1.2 g of white crystals are obtained. The $^1H$ nuclear magnetic resonance spectrum corresponds to the expected trans structure.

Molecular mass found: 338.
Melting point: 152° C.

EXAMPLE 7

Preparation of 4-[cis-2-(1,4-dibromo-5,8-methano-5,6,7,8-tetrahydro-2-naphthyl)propenyl]benzoic acid of formula

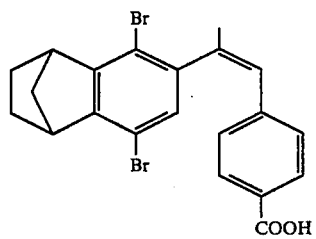

Four drops of crown ether (15C 5) are added at ambient temperature to a stirred solution of 0.5 g of sodium hydride (50% suspension in oil) in 50 cm$^3$ of anhydrous tetrahydrofuran, protected from light and from atmospheric moisture, and then, at a temperature of 10° C., a solution containing the mixture of 3 g of 2-acetyl-1,4-dibromobenzonorbornene and 2.9 g of diethyl 4-ethoxycarbonyl benzylphosphonate is added dropwise. The progress of the reaction mixture is followed by thin-layer chromatography. After 5 hours at ambient temperature 5 cm$^3$ of ethanol are added to destroy a possible residue of unreacted sodium hydride. The reaction mixture is then poured into 200 cm$^3$ of 2N hydrochloric acid and extracted with ethyl ether. The ether phase is dried over magnesium sulphate, and evaporated to dryness.

Ethyl 4-[cis-2-(1,4-dibromo-5,8-methano-5,6,7,8-tetrahydro-2-naphthyl)propenyl]benzoate is obtained as a brown oil which is treated directly at 50° C. in a mixture consisting of 30 cm$^3$ of ethanol and 30 cm$^3$ of 6N potassium hydroxide for 3 hours while protected against light. Ethanol is then evaporated off. The basic aqueous phase is diluted with 100 cm$^3$ of water and extracted three times with ether, which enables some impurities to be extracted.

The aqueous phase is separated by gravity, and then acidified to pH$\simeq$1; a light-yellow precipitate forms. It is filtered off, washed with water and twice with 10-cm$^3$ portions of ether. 1.7 g of 4-[cis-2-(1,4-dibromo-5,8-methano-5,6,7,8-tetrahydro-2-naphthyl)propenyl]benzoic acid are obtained, the structure of which is confirmed by a $^1H$ 250 MHz spectrum. It is a light-beige solid melting at 267° C.

Analysis of the product obtained gives the following results:

| Analysis | Calculated for $C_{21}H_{18}Br_2O_2$ | Found |
|---|---|---|
| C % | 54.57 | 54.32 |
| H % | 3.92 | 3.86 |
| Br % | 34.58 | 34.50 |
| O % | 6.92 | 6.72 |

EXAMPLE 8

Preparation of ethyl 4-[cis-2-(1,4-dibromo-5,8-methano-5,6,7,8-tetrahydro-2-naphthyl)propenyl]benzoate of formula

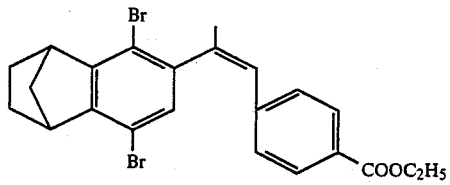

Four drops of crown ether (15C 5) are added at ambient temperature to a stirred solution of 1 g of sodium hydride (50% suspension in oil) in 50 cm³ of anhydrous tetrahydrofuran, protected against light and atmospheric moisture. Then, a solution of 30 cm³ of tetrahydrofuran containing a mixture of 5 g of diethyl 4-ethoxycarbonyl benzylphosphonate and 4.03 g of 2-acetyl-3-isobutylbenzonorbornene is added at ambient temperature.

After 1 hour at the boiling point of tetrahydrofuran, additional 0.5 g of phosphonate is added.

The mixture is stirred further for 4 hours at 70° C. At this stage the reaction is complete. The unreacted sodium hydride is destroyed by adding 5 cm³ of ethanol.

The reaction mixture is then poured into 200 cm³ of water and then extracted with ether. The ether phase is washed, dried and concentrated. The product obtained is purified by chromatography on silica gel and eluted with methylene chloride.

2.5 g of a viscous liquid are obtained, the nuclear magnetic resonance spectrum of which corresponds chiefly to ethyl 4-[cis-2-(3-isobutyl-5,8-methano-5,6,7,8-tetrahydro-2-naphthyl)propenyl]benzoate.

EXAMPLE 10

Preparation of 4-[cis-2-(3-isobutyl-5,8-methano-5,6,7,8-tetrahydro-2-naphthyl)propenyl]benzoic acid

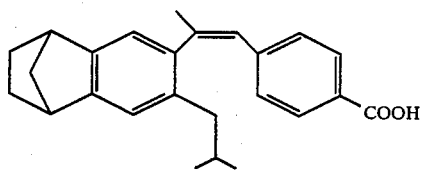

A mixture of 20 cm³ of ethanol, of 20 cm³ of 6N potassium hydroxide and 2 g of the above ester is heated at 50° C. for 2 hours while protected against light. Alcohol is evaporated off, the residual solution is diluted with 100 cm³ of water and extracted twice with 25-cm³ portions of ether.

The aqueous phase is acidified by adding 3N hydrochloric acid and extracted three times with 30-cm³ portions of ether.

The ether phases are combined, dried over magnesium sulphate and concentrated. 1.2 g of acid containing the two cis and trans isomers is obtained. 0.6 g of 4-[cis-2-(3-isobutyl-5,8-methano-5,6,7,8-tetrahydro-2-naphthyl)propenyl]benzoic acid is isolated by crystallization from 10 cm³ of methanol. These are cream-colored crystals the melting point of which is 191° C.

| Analysis | Calculated for $C_{25}H_{28}O_2$ | Found |
| --- | --- | --- |
| C % | 83.29 | 83.09 |
| H % | 7.83 | 7.85 |
| O % | 8.88 | 8.89 |

EXAMPLE 11

Preparation of ethyl 4-[cis-2-(5,8-methano-5,6,7,8-tetrahydro-2-naphthyl)-3-methylbutenyl]benzoate of formula

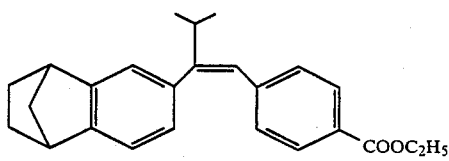

Under experimental conditions identical to those described in Example 7, 3 g of 2-isobutyrylbenzonorbornene and 5 g of diethyl 4-ethoxycarbonyl benzylphosphonate in 50 cm³ of anhydrous tetrahydrofuran are treated with 0.87 g of sodium hydride (50% suspension in oil) in the presence of a few drops of crown ether.

The mixture is heated under reflux for 5 hours and then treated in accordance with Example 7.

After evaporation of the ether extracts, 5 g of the expected product are obtained. It is purified by being passed through a column of silica gel and eluted with a 97/3 hexane/ethyl acetate mixture.

3 g of ethyl 4-[cis-2-(5,8-methano-5,6,7,8-tetrahydro-2-naphthyl)-3-methylbutenyl]benzoate are obtained, the

EXAMPLE 9

Preparation of ethyl 4-[cis-2-(3-isobutyl-5,8-methano-5,6,7,8-tetrahydro-2-naphthyl)propenyl]benzoate of formula

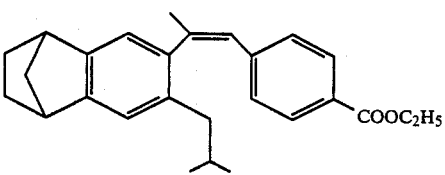

A solution of 0.5 g of the above acid in 30 cm³ of ethanol is heated to reflux in the presence of a gram of para-toluenesulphonic acid under protection against light and in an inert atmosphere. Five hours are necessary to convert all the acid to the corresponding ethyl ester. Ethanol is removed by evaporation under vacuum. The crude ester is dissolved in 50 cm³ of methylene chloride. The solution is washed with potassium bicarbonate and then with water; it is dried over magnesium sulphate and concentrated. The ethyl ester thus obtained is crystallized from methanol. 0.2 g of cream-coloured crystals melting at 79° C. is obtained.

The ¹H 250 MHz nuclear magnetic resonance spectrum confirms the cis structure of the product obtained.

¹H 250 MHz nuclear magnetic resonance spectrum of which confirms the cis structure.

| Analysis | Calculated for $C_{25}H_{28}O_2$ | Found |
|---|---|---|
| C % | 83.29 | 83.27 |
| H % | 7.83 | 7.90 |
| O % | 8.88 | 8.86 |

EXAMPLE 12

Preparation of ethyl 4-[trans-2-(5,8-methano-5,6,7,8-tetrahydro-2-naphthyl)-3-methylbutenyl]benzoate of formula

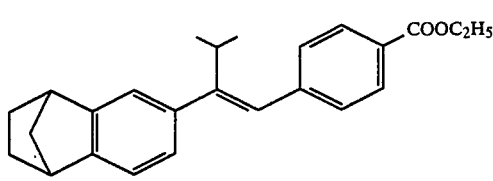

A solution of 3 g of the cis ester prepared in accordance with Example 11 in 400 cm³ of methanol is exposed to natural light. The cis→trans isomerization is followed by H.P.L.C.

After 24 hours' exposure approximately 80% of cis isomer is converted to trans. The solution is concentrated to approximately 50 cm³ and placed at −20° C. The expected trans isomer crystallizes. It is filtered off, dried and analyzed. 2 g of ethyl 4-[trans-2-(5,8-methano-5,6,7,8-tetrahydro-2-naphthyl)-3-methylbutenyl]benzoate are obtained. The trans structure is confirmed by the ¹H 250 MHz nuclear magnetic resonance spectrum. It is a white solid the melting point of which is 65° C.

EXAMPLE 13

Preparation of 4-[trans-2-(5,8-methano-5,6,7,8-tetrahydro-2-naphthyl)-3-methylbutenyl]benzoic acid

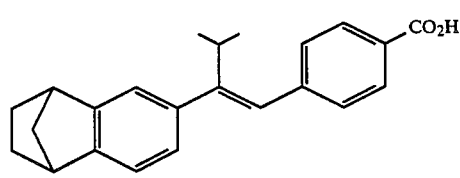

30 cm³ of a 6N aqueous potassium hydroxide solution are added to a suspension of 1 g of the above ester prepared in accordance with Example 12, in 30 cm³ of absolute alcohol. The mixture is stirred for 2 hours at 60° C. while protected from light. At this stage all the ester is saponified. The mixture is poured into 70 cm³ of water and extracted twice with ether. The aqueous phase is then acidified to pH≃1.

The expected acid is extracted with ether. The ether phase is washed, dried over magnesium sulphate, filtered and then concentrated under reduced pressure. The solid obtained is recrystallized from 20 cm³ of methanol at −20° C. The crystals are filtered off and dried. 600 mg of 4-[trans-2-(5,8-methano-5,6,7,8-tetrahydro-2-naphthyl)-3-methylbutenyl]benzoic acid are obtained, the melting point of which is 161° C.

| Analysis | Calculated for $C_{23}H_{24}O_2$ | Found |
|---|---|---|
| C % | 83.10 | 82.98 |
| H % | 7.27 | 7.30 |
| O % | 9.63 | 9.45 |

EXAMPLE 14

Preparation of 4-[cis-2-(1,4-dimethoxy-5,8-methano-5,6,7,8-tetrahydro-2-naphthyl)propenyl]benzoic acid

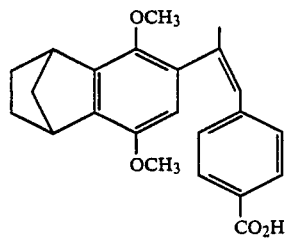

and of its trans isomer

A mixture of 1.05 g of sodium hydride (50% in oil), of a few drops of crown ether 15 crown 5 in 50 cm³ of anhydrous tetrahydrofuran is stirred in an inert atmosphere for half an hour at ambient temperature. Then, at about 10° C., a solution of 4.5 g of 2-acetyl-1,4-dimethoxybenzonorbornene (prepared in accordance with Example G) and of 6 g of diethyl 4-ethoxycarbonyl benzylphosphonate in 50 cm³ of tetrahydrofuran is added dropwise. The mixture is then heated under reflux for 5 hours. 5 cm³ of acetic acid are then added at ambient temperature and the mixture is treated in accordance with Example 1. After purification by passing through a column of silica gel, 4.1 g of ethyl 4-[cis-2-(5,8-methano-5,6,7,8-tetrahydro-2-naphthyl)propenyl]benzoate are obtained as a mixture with its trans isomer. This mixture, dissolved in 40 cm³ of ethanol is treated directly with 40 cm³ of 6N aqueous potassium hydroxide at a temperature of 50° C. until the complete conversion to the corresponding acid. The alcohol is evaporated off. The aqueous phase is extracted once with ether, and then acidified to pH≃1 and reextracted with ether several times. The organic phase is dried and then concentrated. The product obtained is then crystallized from the minimum quantity of acetonitrile. 1 gram of white crystals melting at 212° C. is isolated in this manner. The nuclear magnetic resonance spectrum corresponds to the structure of 4-[cis-2-(1,4-dimethoxy-5,8-methano-5,6,7,8-tetrahydro-2-naphthyl)propenyl]benzoic acid.

To obtain the corresponding trans isomer, the mixture of Z and E isomers obtained after saponification, followed by acidification, is taken up directly in methanol. In this solvent, the trans acid crystallises first.

4-[trans-2-(1,4-Dimethoxy-5,8-methano-5,6,7,8-tetrahydro-2-naphthyl)propenyl]benzoic acid is a white solid melting at 180° C.

EXAMPLE 15

Preparation of all-trans 7-(5,8-methano-5,6,7,8-tetrahydro-2-naphthyl)-3-methyl-2,4,6-heptatrienoic acid

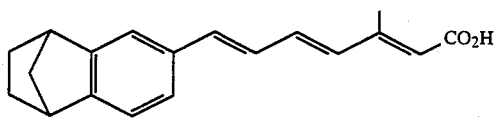

5 g of the phosphonium salt of Example J are suspended in tetrahydrofuran and treated with 6 cm³ of butyllithium (2.5M). After the intensely red solution has been stirred for 2 hours at ambient temperature, 1 cm³ of dichloromethane is added, followed by 1.85 g of ethyl 5-formyl-3-methyl-2,4-pentadienoate in solution in dichloromethane, protected against light. After 1 hour's reaction at ambient temperature, the reaction mixture is hydrolyzed by addition of acetic acid. The solution is concentrated under reduced pressure and the residue is purified by chromatography on silica gel. 3 g of a yellow oil are obtained, the NMR spectrum of which corresponds to a mixture of cis and trans ethyl 7-(5,8-methano-5,6,7,8-tetrahydro-2-naphthyl)-3-methyl-2,4,6-heptatrienoate. This oil is heated at 50° C. in a mixture of 50 cm³ of ethanol and 50 cm³ of 6N potassium hydroxide. Heating is continued (approximately 4 h) until the starting material has completely disappeared. The reaction mixture is concentrated under reduced pressure and acidified with 2N hydrochloric acid. The product obtained is filtered off and crystallized from methanol. 500 mg of a yellow product are recovered, the ¹H 250 MHz NMR spectrum of which corresponds to the expected structure and the melting point of which is 199°-201° C.

EXAMPLE 16

Preparation of all-trans ethyl 7-(1,4-dimethoxy-5,8-methano-5,6,7,8-tetrahydro-2-naphthyl)-3-methyl-2,4,6-octatrienoate

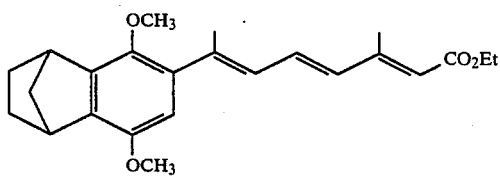

5 cm³ of n-butyllithium (2.5M) are added in an inert atmosphere to a suspension of 5 g of the phosphonium salt of Example H in 100 cm³ of tetraydrofuran. After 2 hours' stirring at ambient temperature, the starting salt is found to have dissolved completely and an intense red coloration is observed. 1.5 g of ethyl 5-formyl-3-methyl-2,4-pentadienoate are then added as a solution in dichloromethane, protected against light. After reaction of the starting aldehyde, the reaction mixture is hydrolyzed with acetic acid. The solution is concentrated under reduced pressure, and the residue is purified by chromatography on silica gel. A pure fraction of a yellow oil is obtained, the ¹H NMR spectrum of which corresponds to the expected all-trans structure.

EXAMPLE 17

Preparation of all-trans 7-(1,4-dimethoxy-5,8-methano-5,6,7,8-tetrahydro-2-naphthyl)-3-methyl-2,4,6-octatrienoic acid

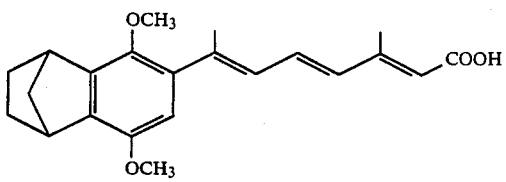

A mixture of 1 g of the ester of Example 16, 25 cm³ of ethanol and 25 cm³ of 6N aqueous potassium hydroxide is heated at 50° C. for approximately 2 hours. After evaporation of the alcohol under reduced pressure, the aqueous phase is acidified with 2N hydrochloric acid and the expected product is extracted with ethyl acetate. After recrystallization from ethanol, 350 mg of a yellow product are recovered, the structure of which in ¹H 250 MHz NMR agrees with the expected all-trans structure and the melting point of which is 193°-195° C.

EXAMPLE 18

The following composition is prepared:

| | |
|---|---|
| Compound of Example 2 | 0.1 g |
| Polyethylene glycol (average molecular weight = 400) | 60.0 g |
| Polyethylene glycol (average molecular weight = 4,000) | 25.0 g |
| Paraffin oil q.s. | 100.0 g |

In this way a suspension forming a water-removable ointment is obtained. This preparation is employed on skins with acne, dermatosis or psoriasis and is applied once to three times daily; good results are obtained over a period of between 6 and 12 weeks depending on the severity of the case treated.

EXAMPLE 19

The following composition is prepared:

| | |
|---|---|
| Compound of Example 1 | 0.15 g |
| Mixture of emulsifiable Lanolin alcohols and waxes and of refined oils based on hydrocarbons sold by B.D.F. Medical under the name of "Eucerin anhydre" | 40.0 g |
| Stabilizers q.s. | |
| Sterile demineralized water q.s. | 100.0 g |

In this way a nonionic suspension forming a cream is obtained. This cream is employed for the treatment of ichthyosis and is applied once to three times daily; good results are obtained over a period of between 6 and 12 weeks depending on the severity of the case treated.

EXAMPLE 20

The following composition is prepared:

| | |
|---|---|
| Compound of Example 3 | 1.0 g |
| Sodium dodecylsulphate | 0.78 g |
| 1,2-Propanediol | 1.56 g |
| Cetyl alcohol | 19.50 g |
| Thick paraffin oil | 19.50 g |
| Stabilizers q.s. | |
| Sterile demineralized water q.s. | 100.00 g |

In this way an anionic suspension forming a cream is obtained. This cream is employed for the treatment of dry acnes and confined patches of psoriasis and is applied once to three times daily; good results are obtained over a period of between 6 and 12 weeks, depending on the severity of the case treated.

EXAMPLE 21

The following composition is prepared:

| | |
|---|---|
| Compound of Example 17 | 0.050 g |
| Wheat starch | 0.265 g |
| Dicalcium phosphate | 0.040 g |
| Lactose ("fine crystals" grade) | 0.040 g |
| Talc | 0.010 g |
| Magnesium stearate | 0.005 g |

In this way 0.4 g tablets are obtained. These tablets are to be taken twice daily for the treatment of rheumatoid psoriasis and a significant improvement is observed after approximately 30 days.

EXAMPLE 22

The following composition is prepared:

| | |
|---|---|
| Compound of Example 16 | 0.05 g |
| Glycerin | 2.40 g |
| 70% Sorbitol | 2.00 g |
| Sucrose | 0.10 g |
| Sodium para-hydroxybenzoate | 0.08 g |
| Flavoring q.s. | |
| Purified water q.s. | 10.00 ml |

In this way a drinkable suspension is obtained which is packaged in 10 ml phials. This drinkable suspension is employed for the treatment of particularly severe cases of acne and of psoriatic rheumatism by one to three ingestions daily; a significant improvement is obtained after approximately 30 days.

EXAMPLE 23

The following composition is prepared:

| | |
|---|---|
| Compound of Example 2 | 0.001 g |
| Sodium chloride | 0.8 g |
| Citric acid/sodium hydroxide buffer q.s. | ph 6 |
| Water for injection q.s. | 100 ml |

In this way a solution is obtained which can be injected by intravenous route. This solution is employed for the treatment of epithelial tumors.

EXAMPLE 24

The following composition is prepared:

| | |
|---|---|
| Compound of Example 13 | 0.1 g |
| Polyethylene glycol (average molecular weight = 400) | 60.0 g |
| Polyethylene glycol (average molecular weight = 4,000) | 25.0 g |
| Paraffin oil q.s. | 100.0 g |

In this way a suspension forming a water-removable ointment is obtained. This preparation is employed on skins with acne, dermatosis or psoriasis and is applied once to three times daily; good results are obtained over a period of between 6 and 12 weeks, depending on the severity of the case treated.

EXAMPLE 25

The following composition is prepared:

| | |
|---|---|
| Compound of Example 14 (trans) | 0.15 g |
| Mixture of emulsifiable lanolin alcohols and waxes and refined oils based on hydrocarbons sold by B.D.F. Medical under the name of "Eucerin anhydre" | 40.0 g |
| Stabilizers q.s. | |
| Sterile demineralized water q.s. | 100.0 g |

In this way a nonionic suspension forming a cream is obtained. This cream is employed for the treatment of ichthyosis and applied once to three times daily; good results are obtained over a period of between 6 and 12 weeks, depending on the severity of the case treated.

EXAMPLE 26

An antiseborrhoeic lotion is prepared in the following manner:

0.1 g of the compound of Example 4 is added to a solution consisting of 10 cm$^3$ of 95° ethanol and 30 cm$^3$ of polyethylene glycol (molecular mass: approximately 400), containing 20 mg of butylated hydroxytoluene.

After dissolution with stirring, the lotion is applied all over the hair.

The treatment is preferably carried out twice daily. After 15 days' treatment a satisfactory result is observed.

EXAMPLE 27

An antiseborrhoeic lotion is prepared in the following manner:

0.1 g of the compound of Example 9 is added to a solution consisting of 10 cm$^3$ of 95° ethanol and 30 cm$^3$ of polyethylene glycol (molecular mass: approximately 400), containing 20 mg of butylated hydroxytoluene.

After dissolution with stirring, the lotion is applied all over the hair.

The treatment is preferably carried out twice daily. After 15 days' treatment a satisfactory result is noted.

EXAMPLE 28

An anti-seborrhoeic cream is prepared by producing the following formulation:

| | |
|---|---|
| Polyoxyethylene stearate (40 moles of ethylene oxide sold under the name "Myrj 52" by "Atlas" | 4 g |
| Mixture of sorbitan and sorbitol laurates, polyoxyethylenated with 20 moles of ethylene oxide, sold under the name "Tween 20" by "Atlas" | 1.8 g |
| Mixture of glycerol mono- and distearate sold under the name "Geleol" by "Gattefosse" | 4.2 g |
| Propylene glycol | 10 g |
| Butylated hydroxyanisole | 0.01 g |
| Butylated hydroxytoluene | 0.02 g |
| Ceto-stearyl alcohol | 6.2 g |
| Preserving agents q.s. | |
| Perhydrosqualene | 18 g |
| Mixture of caprylic-capric triglycerides sold under the name "Miglyol 812" "Dynamit Nobel" | 4 g |
| α-Carboxymethylcysteine | 3 g |
| 99% Triethanolamine | 2.5 g |
| Compound of Example 6 | 0.02 g |
| Water q.s. | 100 g |

EXAMPLE 29

An anti-seborrhoeic cream is prepared by producing the following formulation:

| | |
|---|---|
| Polyoxyethylene stearate (40 moles of ethylene oxide) wold under the name "Myrj 52" by "Atlas" | 4 g |
| Mixture of sorbitan and sorbitol laurates, polyoxyethylenated with 20 moles of ethylene oxide, sold under the name "Tween 20" by "Atlas" | 1.8 g |
| Mixture of glycerol mono- and distearate sold under the name "Geleol" by "Gattefosse" | 4.2 g |
| Propylene glycol | 10 g |
| Butylated hydroxyanisole | 0.01 g |
| Butylated hydroxytoluene | 0.02 g |
| Ceto-stearyl alcohol | 6.2 g |
| Preserving agents q.s | |
| Perhydrosqualene | 18 g |
| Mixture of caprylic-capric triglycerides sold under the name "Miglyol 812" by "Dynamit Nobel" | 4 g |
| 2-Benzylthioethylammonium 5-amino-5-carboxy-3-thiapentanoate | 3 g |
| Compound of Example 2 | 0.02 g |
| Water q.s. | 100 g |

EXAMPLE 30

An anhydrous lotion is prepared by mixing the following ingredients:

| | |
|---|---|
| Ethanol | 45 g |
| Propylene glycol | 44.05 g |
| Polytetrahydrofuran dimethyl ether | 10 g |
| Compound of Example 3 | 0.1 g |
| Butylated hydroxytoluene | 0.05 g |

EXAMPLE 31

A screening gel is prepared by mixing the following ingredients:

| | |
|---|---|
| Ethyl alcohol | 44 g |
| Propylene glycol | 44.15 g |
| Acrylic acid polymer sold under the name "Carbopol 940" by "Goodrich Chemical Co." | 1 g |
| 99% Triethanolamine | 0.5 g |
| Butylated hydroxyanisole | 0.01 g |
| Butylated hydroxytoluene | 0.02 g |
| Purified water | 10 g |
| Compound of Example 15 | 0.02 g |
| 3,3'-Terephthalylidene-10,10'-dicamphosulphonic acid dihydrate | 0.5 g |

EXAMPLE 32

An anti-acne cream is prepared by mixing the following ingredients:

| | |
|---|---|
| Mixture of glycerol and polyethylene glycol (75 mol) stearates sold under the name "Gelot 64" by "Gattefosse" | 15 g |
| Kernel oil polyoxyethylenated with 6 moles of ethylene oxide, sold under the name "Labrafil M 2130 CS" by "Gattefosse" | 8 g |
| Perhydrosqualene | 10 g |
| Colorant q.s. | |
| Preserving agents q.s. | |
| Perfumes q.s. | |
| Thioxolone | 0.4 g |
| Polyethylene glycol of molecular mass 400 | 8 g |
| Purified water | 58.5 g |
| Disodium ethylenediaminetetraacetate | 0.05 g |
| Compound of Example 2 | 0.05 g |

EXAMPLE 33

A lotion of regrowth of hair is prepared by mixing the following ingredients:

| | |
|---|---|
| Propylene glycol | 20 g |
| Ethanol | 34.92 g |
| Polyethylene glycol of molecular mass 400 | 40 g |
| Water | 4 g |
| Butylated hydroxyanisole | 0.01 g |
| Butylated hydroxytoluene | 0.02 g |
| Compound of Example 2 | 0.05 g |
| Minoxidil | 1 g |

EXAMPLE 34

An anti-acne cream is prepared by mixing the following ingredients:

| | |
|---|---|
| Polyoxyethylene stearate (40 mol of ethylene oxide) sold under the name of "Myrj 52" by "Atlas" | 4 g |
| Mixture of sorbitan and sorbitol laurates, polyoxyethylenated with 20 moles of ethylene oxide, sold under the name "Tween 20" by "Atlas" | 1.8 g |
| Mixture of glycerol mono- and distearate sold under the name "Geleol" by "Gattefosse" | 4.2 g |
| Propylene glycol | 10 g |
| Butylated hydroxyanisole | 0.01 g |
| Butylated hydroxytoluene | 0.02 g |
| Ceto-stearyl alcohol | 6.2 g |
| Preserving agents q.s. | |
| Polytetrahydrofuran dimethyl ether | 18 g |
| Mixture of caprylic-capric triglycerides sold under the name "Miglyol 812" by "Dynamit Nobel" | 4 g |
| Compound of Example 2 | 0.02 g |
| Water q.s. | 100 g |

EXAMPLE 35

An anti-acne gel is prepared by producing the following formulation:

| | |
|---|---|
| Compound of Example 2 | 0.05 g |
| Isopropyl alcohol | 40 g |
| Acrylic acid polymer sold under the name "Carbopol 940" by "Goodrich Chemical Co" | 1 g |
| 99% Triethanolamine | 0.6 g |
| Butylated hydroxyanisole | 0.01 g |
| Butylated hydroxytoluene | 0.02 g |
| Thioxolone | 0.5 g |
| Propylene glycol | 8 g |
| Purified water q.s. | 100 g |

EXAMPLE 36

A screening cream is prepared by producing the following formulation:

| | |
|---|---|
| Polyoxyethylene stearate (40 moles of ethylene oxide) sold under the name "Myrj 52" by "Atlas" | 4.4 g |
| Ceto-stearyl alcohol | 6.2 g |
| Mixture of glycerol mono-and distearate sold under the name "Geleol" by "Gattefosse" | 4.3 g |
| Butylated hydroxyanisole | 0.05 g |
| Butylated hydroxytoluene | 0.05 g |
| Xanthane gum | 0.25 g |
| Isopropyl myristate | 4 g |
| Compound of Example 10 | 0.1 g |

-continued

| | |
|---|---|
| 3,3'-Terephthalylidene-10,10'-dicamphosulphonic acid dihydrate | 2 g |
| 99% Triethanolamine | 1 g |
| Demineralized water q.s. | 100 g |

EXAMPLE 37

This is an anti-acne kit comprising two parts:
(a) a gel is prepared by producing the following formulation:

| | |
|---|---|
| Ethyl alcohol | 48.4 g |
| Propylene glycol | 50 g |
| Acrylic acid polymer sold under the name "Carbopol 940" by "Goodrich Chemical Co" | 1 g |
| 99% Diisopropanolamine | 0.3 g |
| Butylated hydroxyanisole | 0.05 g |
| Butylated hydroxytoluene | 0.05 g |
| α-Tocopherol | 0.1 g |
| Compound of Example 3 | 0.1 g |

(b) a gel is prepared by producing the following formulation:

| | |
|---|---|
| Ethyl alcohol | 5 g |
| Propylene glycol | 5 g |
| Disodium ethylenediaminetetraacetate | 0.05 g |
| Acrylic acid polymer sold under the name "Carbopol 940" by "Goodrich Chemical Co" | 1 g |
| 99% Triethanolamine | 1 g |
| Sodium laurylsulphate | 0.1 g |
| Purified water | 75.05 g |
| 25% Aqueous benzoyl peroxide | 12.8 g |

A mixture of the two gels, weight for weight, is made at the time of use.

It is obvious that the examples of implementation described above are not restrictive in any manner and may give rise to all desirable modifications, without departing thereby from the scope of the invention.

We claim:

1. A process for the preparation of a benzonorbornene derivative of formula (I), or an isomer or salt thereof, wherein formula (I) is (I)

wherein
$R_1$, $R_3$ and $R_4$ each independently represent hydrogen, $C_1$-$C_8$ alkyl, $C_1$-$C_8$ alkoxy, halogen, $C_1$-$C_8$ acyloxy or hydroxyl,
$R'$ is hydrogen or $C_1$-$C_6$ alkyl, and $R''$ is a polyene having formula (II)

(II)

wherein $A_2$ is $CH_2OR_6$ wherein $R_6$ is hydrogen or $C_1$-$C_6$ alkyl, or —$COR_7$ wherein $R_7$ is hydrogen, $C_1$-$C_6$ alkoxy, aryloxy, benzyloxy, a sugar residue, substituted or unsubstituted amino, $C_1$-$C_6$ alkyl or hydroxyl, said process comprising reacting a substituted or unsubstituted 2-acyl benzonorbornene of formula (VII)

(VII)

wherein $R'$, $R_1$, $R_3$ and $R_4$ are defined above with a dialkyl phosphonate of formula (VIII)

(VIII)

wherein
$R_{12}$ is $C_1$-$C_6$ alkyl and
$R''$ is defined above, or with a triphenylphosphonium salt of formula (IX)

$$(C_6H_5)_3P^{\oplus}-CH_2-R''X^{\ominus} \quad (IX)$$

wherein
$R''$ is defined above and
$X^{\ominus}$ is a halide, and
the resulting product is isomerized and/or salified if necessary.

2. A process according to claim 1 in which the compound of formula (VII) is prepared by a process in which a substituted benzonorbornene of formula (VI)

(VI)

is prepared, where $R_1$, $R_3$ and $R_4$ are each independently hydrogen, $C_1$-$C_8$ alkyl, $C_1$-$C_8$ alkoxy, halogen, $C_1$-$C_8$ acyloxy or hydroxyl, which compound is then acylated, in the presence of aluminum chloride, with an acyl chloride R'COCl in which R' is hydrogen or $C_1$-$C_6$ alkyl, to give a compound of formula (VII).

3. A process according to claim 1 in which the compound of formula (VII) is prepared by a process in which benzonorbornene is acylated with an acyl chloride R'COCl or its acid anhydride in which R' is hydrogen or $C_1$-$C_6$ alkyl, causing the group R'—CO— to appear in the 2 position on the benzonorbornene ring and then substitutions are carried out causing the groups $R_1$, $R_3$ and $R_4$ to appear respectively in the 1, 3 and 4 positions in the benzonorbornene ring, $R_1$, $R_3$ and $R_4$ being each independently hydrogen, $C_1$-$C_8$ alkyl, $C_1$-$C_8$ alkoxy, halogen, $C_1$-$C_8$ acyloxy or hydroxyl.

4. A process according to claim 1 for the preparation of a compound of formula (VII) which comprises cyclo-addition of a benzyne of formula (XXV)

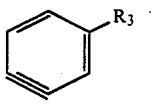 (XXV)

where R₃ is hydrogen, $C_1$–$C_8$ alkyl, $C_1$–$C_8$ alkoxy, halogen, $C_1$–$C_8$ acyloxy or hydroxyl, to cyclo-pentadiene, to give a benzonorbornene of formula (XXIII)

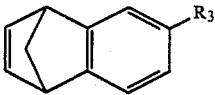 (XXIII)

which is reduced to a benzonorbornene of formula (XXIV)

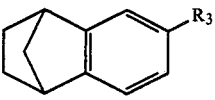 (XXIV)

which compound is acylated with an acyl chloride R'COCl, in the presence of aluminum chloride, R' being hydrogen or $C_1$–$C_6$ alkyl.

5. A process according to claim 1 in which the compound of formula (VII) is prepared by a process in which a substituted benzonorbornene of formula (VI)

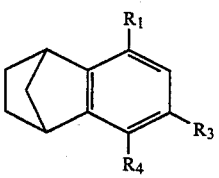 (VI)

is prepared, where R₁, R₃ and R₄ are each independently hydrogen, $C_1$–$C_8$ alkyl, $C_1$–$C_8$ alkoxy, halogen, $C_1$–$C_8$ acyloxy or hydroxyl, which compound is then acylated, in the presence of aluminum chloride, with an acyl chloride R'COCl in which R' is hydrogen or $C_1$–$C_6$ alkyl, to give a compound of formula (VII).

6. A process according to claim 1 in which the compound of formula (VII) is prepared by a proces in which benzonorbornene is acylated with an acylchloride R'COCl or its acid anhydride in which R' is hydrogen or $C_1$–$C_6$ alkyl, causing the group R'—CO— to appear in the 2 position on the benzonorbornene ring and then substitutions are carried out causing the groups R₁, R₃ and R₄ to appear respectively in the 1, 3 and 4 positions in the benzonorbornene ring, R₁, R₃ and R₄ being each independently hydrogen, $C_1$–$C_8$ alkyl, $C_1$–$C_8$ alkoxy, halogen, $C_1$–$C_8$ acyloxy or hydroxyl.

7. A process according to claim 1 for the preparation of a compound of formula (VII) which comprises cyclo-addition of a benzyne of formula (XXV)

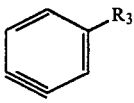 (XXV)

where R₃ is hydrogen, $C_1$–$C_8$ alkyl, $C_1$–$C_8$ alkoxy, halogen, $C_1$–$C_8$ acyloxy or hydroxyl, to cyclo-pentadiene, to give a benzonorbornene of formula (XXIII)

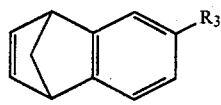 (XXIII)

which is reduced to a benzonorbornene of formula (XXIV)

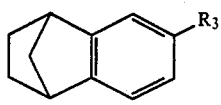 (XXIV)

which compound is acylated with an acyl chloride R'COCl, in the presence of aluminum chloride, R' being hydrogen or $C_1$–$C_6$ alkyl.

8. A process for the preparation of a benzonorbornene derivative of formula (I), or an isomer or salt thereof, having the formula

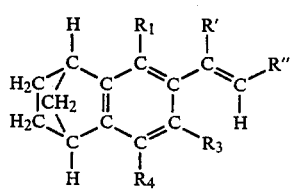 (I)

wherein
R₁, R₃ and R₄ each independently represent hydrogen, $C_1$–$C_8$ alkyl, $C_1$–$C_8$ alkoxy, halogen, $C_1$–$C_8$ acyloxy or hydroxyl,
R' is hydrogen or $C_1$–$C_6$ alkyl, and R" is a polyene having formula (II)

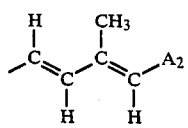 (II)

wherein A₂ is CH₂OR₆ wherein R₆ is hydrogen or $C_1$–$C_6$ alkyl, or —COR₇ wherein R₇ is hydrogen, $C_1$–$C_6$ alkoxy, aryloxy, benzyloxy, a sugar residue, substituted or unsubstituted amino, $C_1$–$C_6$ alkyl or hydroxyl, said process comprising reducing a substituted or unsubstituted 2-acyl benzonorbornene of formula (VII)

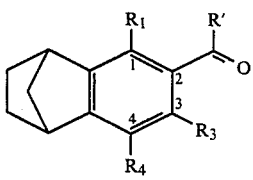 (VII)

wherein R', R₁, R₃ and R₄ are defined above with sodium borohydride so as to form a secondary alcohol of formula (X)

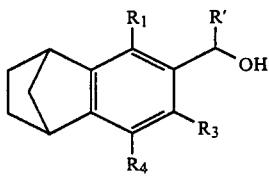

wherein R', R$_1$, R$_3$ and R$_4$ are defined above;
converting the compound of formula (X) by the action of phosphorous tribromide to a bromide of formula (XI)

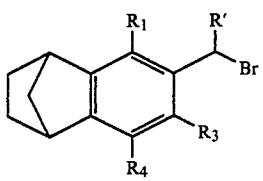

wherein R', R$_1$, R$_3$ and R$_4$ are defined above;
reacting the compound of formula (XI) with triphenyl phosphine so as to obtain a triphenyl phosphonium bromide of formula (XII)

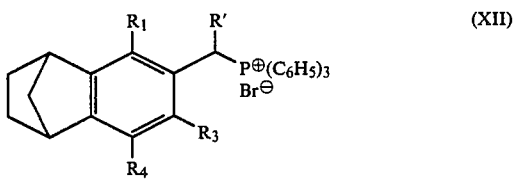

wherein R', R$_1$, R$_3$ and R$_4$ are defined above; and
reacting the compound of formula (XII) with an aldehyde R"CHO wherein R" is defined above so as to obtain a compound of formula (I), which is then isomerized and/or salified if necessary.

9. A process for the preparation of a benzonorbornene derivative of formula (I), or an isomer or salt thereof, wherein formula (I) is

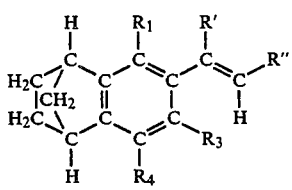

wherein
R$_1$, R$_3$ and R$_4$ each independently represent hydrogen, C$_1$-C$_8$ alkyl, C$_1$-C$_8$ alkoxy, halogen, C$_1$-C$_8$ acyloxy or hydroxyl,
R' is hydrogen or C$_1$-C$_6$ alkyl, and
R" is (i) a polyene having formula (II)

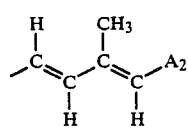

wherein A$_2$ is (a) CH$_2$OR$_6$ wherein R$_6$ is hydrogen or C$_1$-C$_6$ alkyl, or (b) —COR$_7$ wherein R$_7$ is hydrogen, C$_1$-C$_6$ alkoxy, aryloxy, benzyloxy, sugar residue, substituted or unsubstituted amino, C$_1$-C$_6$ alkyl or hydroxyl, or (ii) a benzene ring of formula (III)

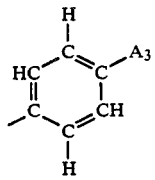

wherein A$_3$ is A$_2$ defined above or hydrogen, C$_1$-C$_6$ alkyl, alkylhtio (—SR$_5$), alkylsulphinyl

or alkylsulphonyl (—SO$_2$R$_5$) wherein R$_5$ is C$_1$-C$_6$ alkyl; with the proviso that if R' is hydrogen or methyl, R$_1$=R$_4$=H and R$_3$ is H or methyl, R" cannot be a benzene ring of formula (III) wherein A$_3$ is —COR$_7$ wherein R$_7$ is OH, alkoxy, aryloxy or —NR$_{10}$R$_{11}$ wherein R$_{10}$ is linear or branched alkyl, substituted or unsubstituted by OH and R$_{11}$ is hydrogen or linear or branched alkyl substituted or unsubstituted by OH, said process comprising reacting a substituted or unsubstituted 2-acyl benzonorbornene of formula (VII)

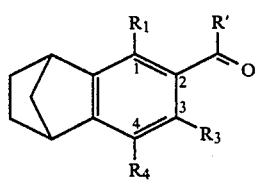

wherein R', R$_1$, R$_3$ and R$_4$ are defined above with a dialkyl phosphonate of formula (VIII)

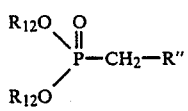

wherein
R$_{12}$ is C$_1$-C$_6$ alkyl and
R" is defined above, or
with a triphenylphosphonium salt of formula (IX)

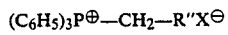

(C$_6$H$_5$)$_3$P$^\oplus$—CH$_2$—R"X$^\ominus$  (IX)

wherein
R" is defined above and
X$^\ominus$ is halide, and the resulting product is isomerized and/or salified if necessary.

10. A process for the preparation of a benzonorbornene derivative of formula (I), or an isomer or salt thereof, wherein formula (I) is

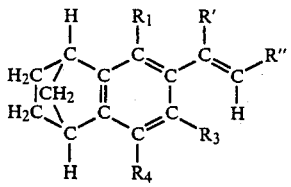 (I)

wherein
$R_1$, $R_3$ and $R_4$ each independently represent hydrogen, $C_1$–$C_8$ alkyl, $C_1$–$C_8$ alkoxy, halogen, $C_1$–$C_8$ acyloxy or hydroxyl,
R' is hydrogen or $C_1$–$C_6$ alkyl, and
R" is (i) a polyene having formula (II)

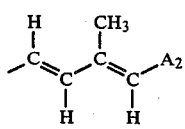 (II)

wherein $A_2$ is (a) $CH_2OR_6$ wherein $R_6$ is hydrogen or $C_1$–$C_6$ alkyl, or (b) —$COR_7$ wherein $R_7$ is hydrogen, $C_1$–$C_6$ alkoxy, aryloxy, benzyloxy, a sugar residue, substituted or unsubstituted amino, $C_1$–$C_6$ alkyl or hydroxyl, or
(ii) a benzene ring of formula (III)

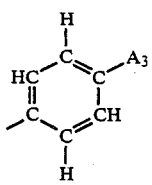 (III)

wherein $A_3$ is $A_2$ defined above or hydrogen, $C_1$–$C_6$ alkyl, alkylthio (—$SR_5$), alkylsulphinyl

or alkylsulphonyl (—$SO_2R_5$) wherein $R_5$ is $C_1$–$C_6$ alkyl; with the proviso that if R' is hydrogen or methyl, $R_1=R_4=H$ and $R_3$ is H or methyl, R" cannot be a benzene ring of formula (III) wherein $A_3$ is —$COR_7$ wherein $R_7$ is OH, alkoxy, aryloxy or —$NR_{10}R_{11}$ wherein $R_{10}$ is linear or branched alkyl, substituted or unsubstituted by OH and $R_{11}$ is hydrogen or linear or branched alkyl substituted or unsubstituted by OH, said process comprising reducing a substituted or unsubstituted 2-acyl benzonorbornene of formula (VII)

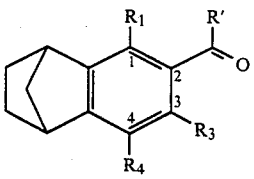 (VII)

wherein R', $R_1$, $R_3$ and $R_4$ are defined above, with sodium borohydride so as to form a secondary alcohol of formula (X)

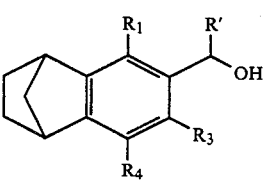 (X)

wherein R', $R_1$, $R_3$ and $R_4$ are defined above,
converting the compound of formula (X) by the action of phosphorus tribromide to a bromide of formula (XI)

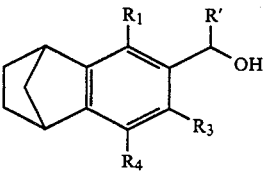 (XI)

wherein R', $R_1$, $R_3$ and $R_4$ are defined above;
reacting the compound of formula (XI) with triphenylphosphine so as to obtain a triphenylphosphonium bromide of formula (XII)

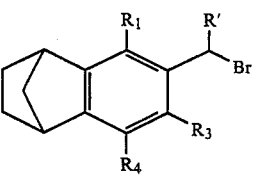 (XII)

wherein R', $R_1$, $R_3$ and $R_4$ are defined above; and
reacting the compound of formula (XII) with an aldehyde R"CHO in which R" is defined above so as to obtain a compound of formula (I) which is then isomerized and/or salified if necessary.

* * * * *